United States Patent
Pai et al.

(10) Patent No.: US 11,160,993 B2
(45) Date of Patent: Nov. 2, 2021

(54) CONTROL METHOD FOR LIGHT THERAPY DEVICE

(71) Applicant: GCSOL TECH CO., LTD., Taichung (TW)

(72) Inventors: Jui-Fen Pai, Nantou (TW); Chen-Ping Kuo, Taichung (TW)

(73) Assignee: GCSOL TECH CO., LTD., Taichung (TW)

( * ) Notice: Subject to any disclaimer, the term of this patent is extended or adjusted under 35 U.S.C. 154(b) by 168 days.

(21) Appl. No.: 16/549,755

(22) Filed: Aug. 23, 2019

(65) Prior Publication Data

US 2020/0069963 A1 Mar. 5, 2020

(30) Foreign Application Priority Data

Sep. 5, 2018 (TW) .................................. 107131058

(51) Int. Cl.
*A61N 5/06* (2006.01)
*A61N 5/067* (2006.01)

(52) U.S. Cl.
CPC .............. *A61N 5/062* (2013.01); *A61N 5/067* (2021.08); *A61N 2005/0626* (2013.01);
(Continued)

(58) Field of Classification Search
CPC .............................. A61N 5/062; A61B 18/203
See application file for complete search history.

(56) References Cited

U.S. PATENT DOCUMENTS

| 5,595,568 A * | 1/1997 | Anderson | A61B 18/203 606/9 |
| 6,413,267 B1 * | 7/2002 | Dumoulin-White | A61N 5/0616 128/898 |

(Continued)

FOREIGN PATENT DOCUMENTS

| CN | 203989512 U | 12/2014 |
| CN | 105263577 A | 1/2016 |

(Continued)

OTHER PUBLICATIONS

"What is the conversion from Lux to W/cm2" (Year: 2020).*

(Continued)

*Primary Examiner* — Lynsey C Eiseman
(74) *Attorney, Agent, or Firm* — Tracy M Heims; Apex Juris, pllc.

(57) ABSTRACT

A control method for a light therapy device, including steps of: set a light dose range (1-4J/cm$^2$) required by an illuminated portion under a skin surface; calculate an appropriate intensity range outputted by a light source based on the set light dose, an illuminated time, and a proportion of light beam shape variation between the light source and the skin surface; build a corresponding relation between the appropriate intensity range and an ideal illumination range for the skin surface; measure an illumination of the skin surface, and monitor an output light intensity of the light source based on the illumination, ensuring that a light intensity outputted by the light source is a set ideal light intensity whereby, a light dose transmitted from the light therapy device to the illuminated portion could be kept in the set light dose by simply controlling the illumination to be within the set illumination range.

9 Claims, 5 Drawing Sheets

(52) U.S. Cl.
CPC ............... *A61N 2005/0652* (2013.01); *A61N 2005/0659* (2013.01); *A61N 2005/0661* (2013.01)

(56) References Cited

U.S. PATENT DOCUMENTS

| | | | | |
|---|---|---|---|---|
| 6,529,543 | B1* | 3/2003 | Anderson | A61B 18/203 372/108 |
| 8,268,332 | B2* | 9/2012 | Manstein | A61P 17/00 424/400 |
| 8,518,094 | B2 | 8/2013 | Wang | |
| 9,802,060 | B2 | 10/2017 | Olds et al. | |
| 9,913,993 | B2 | 3/2018 | Gross et al. | |
| 2007/0100401 | A1* | 5/2007 | Lin | A61B 18/203 607/89 |
| 2007/0213792 | A1* | 9/2007 | Yaroslavsky | A61N 5/0613 607/100 |
| 2008/0287930 | A1* | 11/2008 | Rapoport | B23K 26/0096 606/9 |
| 2012/0071867 | A1* | 3/2012 | Ryan | A61B 18/24 606/15 |
| 2012/0150044 | A1 | 6/2012 | Kim | |
| 2013/0295015 | A1* | 11/2013 | Deisseroth | A01K 67/0275 424/9.2 |

FOREIGN PATENT DOCUMENTS

| | | |
|---|---|---|
| CN | 106390298 A | 2/2017 |
| CN | 107362457 A | 11/2017 |
| CN | 107735146 A | 2/2018 |
| CN | 107929950 A | 4/2018 |
| CN | 108295379 A | 7/2018 |
| KR | 20160049262 A | 5/2016 |
| TW | I633906 B | 9/2018 |
| WO | 2012011042 A2 | 1/2012 |

OTHER PUBLICATIONS

English abstract for CN105263577, Total of 1 page.
English abstract for CN106390298, Total of 1 page.
English abstract for CN107362457, Total of 1 page.
English abstract for CN107735146, Total of 1 page.
English abstract for CN107929950, Total of 1 page.
English abstract for CN108295379, Total of 1 page.
English abstract for CN203989512, Total of 1 page.
English abstract for KR20160049262, Total of 1 page.
English abstract for TWI633906, Total of 1 page.
Search report for TW107131058, dated Jul. 18, 2019, Total of 1 page.
Search report for CN201910571626.0, dated Dec. 16, 2020, Total of 2 page.

* cited by examiner

CONTROL METHOD FOR LIGHT THERAPY DEVICE

BACKGROUND OF THE INVENTION

Technical Field

The present disclosure relates to a light therapy device, and more particularly to a control method for a light therapy device.

Description of Related Art

With the advancement in medicine and technology, a light therapy device has been developed recently, which uses light to illuminate an illuminated portion of a human body (e.g. a hypodermis or a tissue under a skin surface) to induce a biological response to the human body for therapeutic purposes. The light therapy device is a non-invasive treatment, and is a very safe treatment compared to invasive treatments such as acupuncture.

A conventional method of controlling the light therapy device to illuminate to the illuminated portion of the human body by simply controlling the light source to output a certain light intensity and controlling an illuminated time. However, since the light is transmitted under the skin surface of the human body, the light interacts with the tissue under the skin surface to absorb, scatter, refract, etc., so that the tissue of the illuminated portion cannot obtain a suitable light dose. With too lower light dose, the purpose of treatment cannot be achieved; with too high light dose, the illuminated portion may be damaged.

In all aspects, the conventional light therapy device still has room for improvements.

BRIEF SUMMARY OF THE INVENTION

In view of the above, the primary objective of the present disclosure is to provide a control method of a light therapy device, thereby light emitted from the light therapy device could effectively treat an illuminated portion.

The present disclosure provides a control method for a light therapy device, wherein the light therapy device includes a light source. The light source is controllable to change a light intensity outputted by the light source. The control method includes steps of:

A. set a light dose range required by an illuminated portion which is under a skin surface of a human body;

B. calculate an appropriate intensity range outputted by the light source based on the light dose range, an illuminated time, and a proportion of light beam shape variation between the light source and the skin surface above the illuminated portion;

C. build a corresponding relation between the appropriate intensity range and an ideal illumination range for the skin surface above the illuminated portion;

D. measure an illumination corresponding to the skin surface above the illuminated portion, and obtain an output light intensity of the light source corresponding to the measured illumination based on the measured illumination and the corresponding relation;

E. control the light source based on the output light intensity obtained in step D and the appropriate intensity range in step B, thereby the light source outputs the light intensity which is in accordance with the appropriate intensity range.

By setting the light dose required by the illuminated portion, and calculating the appropriate intensity range to be outputted by the light source, and adjusting the light intensity outputted by the light source by monitoring the illumination of the skin surface, the disclosure of the present invention could ensure that the light dose received by the illuminated portion under the skin surface is within the appropriate range.

BRIEF DESCRIPTION OF THE SEVERAL VIEWS OF THE DRAWINGS

The present disclosure will be best understood by referring to the following detailed description of some illustrative embodiments in conjunction with the accompanying drawings, in which.

DETAILED DESCRIPTION OF THE INVENTION

Figure 1:
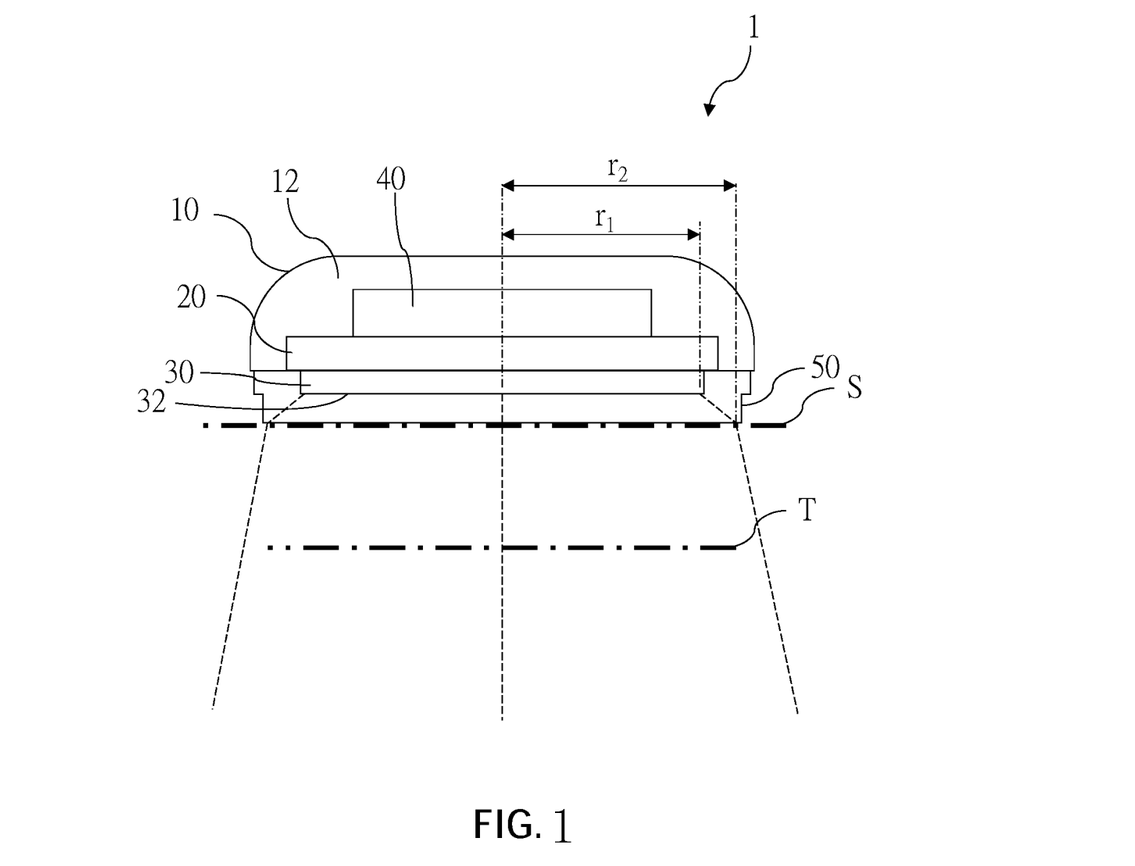
FIG. 1 is a schematic view of the light therapy device according to a first embodiment of the present disclosure.

A control method for a light therapy device according to a first embodiment of the present disclosure is applied to a light therapy device 1 illustrated in FIG. 1, wherein the light therapy device 1 includes a body 10, a control circuit 20, a light source 30, a battery 40, and a uniform light cover 50.

The body 10 has a receiving space 12 inside. The control circuit 20 is disposed in the receiving space 12 of the body 10. The light source 30 is engaged with a side of the control circuit 20, and has a light-emitting surface 32. In the current embodiment, the light source 30 includes a plurality of light-emitting diodes (LEDs), wherein each of the LEDs is a red LED with a wavelength of 600 nm-650 nm. The light-emitting surface 32 is an equivalent light-emitting surface formed by the LEDs. The control circuit 20 is controllable to adjust a light intensity outputted by the light source 30. The battery 40 is connected to another side of the control circuit 20 for supplying electricity to the control circuit 20 and the light source 30. The uniform light cover 50 is engaged with the body 10 and is located on a side of the light-emitting surface 32 of the light source 30, and is adapted to allow light emitted by the light-emitting surface 32 evenly shining through. In the current embodiment, an outer surface of the uniform light cover 50 is adapted to be abutted by a skin surface S of a human body, wherein light penetrating to an illuminated portion T under the skin surface S through the skin surface S. In practice, the light source could be an area light source formed by an OLED to be as a light-emitting surface, wherein the uniform light cover 50 could be omitted when using the OLED as the light source.

Figure 2:
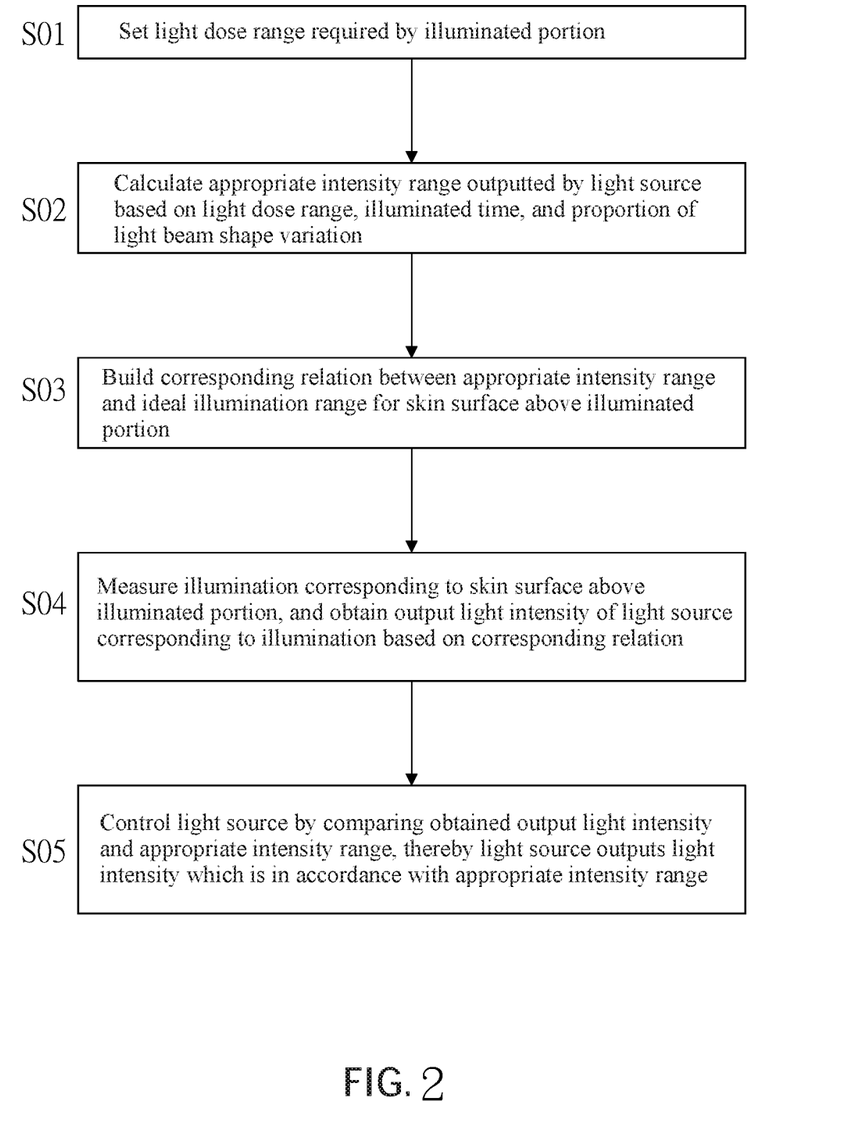
FIG. 2 is a flowchart of the control method of the light therapy device according to the first embodiment of the present disclosure.

The control method according to the current embodiment includes following steps as illustrated in FIG. 2.

Step S01, first, a light dose range required by the illuminated portion T of the human body is set. The light therapy device 1 achieves a therapeutic effect by emitting a light with a specific wavelength to the human body, and the illuminated surface T (for example, injured tissue) of the human body under the skin surface S absorbs the light. In addition to the wavelength, an amount of the light dose is an important factor of therapeutic performance. For example, with too low a light dose, the treatment is ineffective; with too high a light dose, the illuminated portion T of the skin surface S may be damaged. Therefore, a suitable light dose range should be determined for therapeutic purposes. In the current embodiment, factoring in light loss of the illuminated portion T at a predetermined distance below the skin surface S determines the light dose range suitable for repairing the injured tissue under the skin surface S and on the skin surface S while minimizing damage to illuminated portion T. Preferably, treating the injured tissue which is under the skin surface S as the illuminated portion T a light dose range of 1-4 J/cm$^2$ in a red light wavelength range. A rate of light loss increases with a distance between the skin surface S and the illuminated portion T under the skin surface S. For example, the rate of light loss when the distance between the skin surface S and the illuminated portion T is less than 1 mm is 40%, the light dose on the skin surface S results in a light dose range of 1.67-6.67 J/cm$^2$ (i.e., 1/(1-40%) to 4/(1-40%) J/cm$^2$). As another example, when the distance between the skin surface S and the illuminated portion T is about 3 mm, the rate of light loss is 90%, the light dose on the skin surface S results in a light dose range of 1040 J/cm$^2$ (i.e., 1/(90%) to 4/(1-90%) J/cm$^2$). In practice, a suitable light dose range could be determined depending on different illuminated portions T and different wavelengths of light source 30.

Step S02, after determining the light dose range, an appropriate intensity range that the light source 30 should output could be calculated based on the light dose range, an illuminated time, and a proportion of light beam shape variation between the light source 30 and the skin surface S above the illuminated portion T. The calculated appropriate intensity range outputted by the light source 30 could ensure the light dose range of the illuminated portion T (e.g. the injured tissue) under the skin surface S meets the set light dose range of 1-4 J/cm$^2$. In the current embodiment, the appropriate intensity range is 0.275-6.6 mW/cm$^2$. Preferably, considering that it could be applied to both of the illuminated portion T which is close to the skin surface S and the illuminated portion T which is away from the skin surface S and is under the skin surface S, the appropriate intensity range is 1.1-1.65 mW/cm$^2$.

The appropriate intensity range is calculated based on a following equation:

$$P = \frac{D_t}{(1-\varepsilon)\times t} \times \left(\frac{r_2}{r_1}\right)^2 \times 1000$$

wherein P is an ideal light intensity of the light source 30 within the appropriate intensity range, and a unit thereof is mW/cm$^2$; Dt is a light dose within the light dose range, and a unit thereof is J/cm$^2$; $\varepsilon$ is a rate of light loss at a specific distance under the skin surface S; t is the illuminated time; r1 is a radius of a light beam emitted by the light-emitting surface 32 of the light source 30; r2 is a radius of a light beam on the skin surface S above the illuminated portion T. A ratio of r2 to r1 is the proportion of light beam shape variation between the light source 30 and the skin surface S above the illuminated portion T. By respectively substituting Dt into 1 J/cm$^2$ and 4 J/cm$^2$, an upper bound and a lower bound of the ideal light intensity P of the light source 30 are obtained, which constitute the appropriate intensity range.

In addition to using the radius of the light beam as a basis for calculation, an area of the light beam could also be used as a basis for calculation as shown in a following equation:

$$P = \frac{D_t}{(1-\varepsilon)\times t} \times \frac{A_2}{A_1} \times 1000$$

wherein A1 is an area of a light beam emitted by the light-emitting surface 32 of the light source 30; A2 is an area of a light beam on the skin surface S above the illuminated portion T. A ratio of A2 to A1 is the proportion of light beam shape variation between the light source 30 and the skin surface S above the illuminated portion T.

For divergent beams such as LEDs and OLED light source, r2>r1 (A2>A1); for parallel beams such as laser light source, r2=r1 (A2=A1).

Hence, one of the above-mentioned equations and the parameters used therein could be set in the control circuit 20, so that the control circuit 20 could figure out the appropriate intensity range of the light source 30. In practice, before calculating the appropriate intensity range of the light source, the rate of light loss at different specific distances between the skin surface S to the illuminated portion T could be built in the control circuit 20 in advance, wherein the required specific distance for the desired treatment could be selected via the control circuit 20. In this way, the appropriate intensity range of different light source 30 could be obtained based on different specific distances.

Step S03, a corresponding relation between the skin surface S above the illuminated portion T and an ideal illumination range for the skin surface S above the illuminated portion T within the appropriate intensity range of the light source 30 is built. In the current embodiment, the corresponding relation is built by establishing a relation between a plurality of different predetermined illuminations for the skin surface S above the illuminated portion T and a plurality of predetermined output light intensities corresponding to the predetermined illuminations, wherein the appropriate intensity range of the light source 30 includes the predetermined output light intensities; the ideal illumination range includes the predetermined illuminations.

In the current embodiment, the corresponding relation is built during the appropriate intensity range of the light source 30 by measuring each of the predetermined output light intensities and each of the predetermined illuminations corresponding to the predetermined output light intensities, wherein a form of the corresponding relation could be a relation table, a relation equation, or a relation diagram. The corresponding relation could be built in advance and be stored into a memory. In the current embodiment, the memory is disposed in a test device 70 which is located out of the light therapy device 1.

Figure 3:
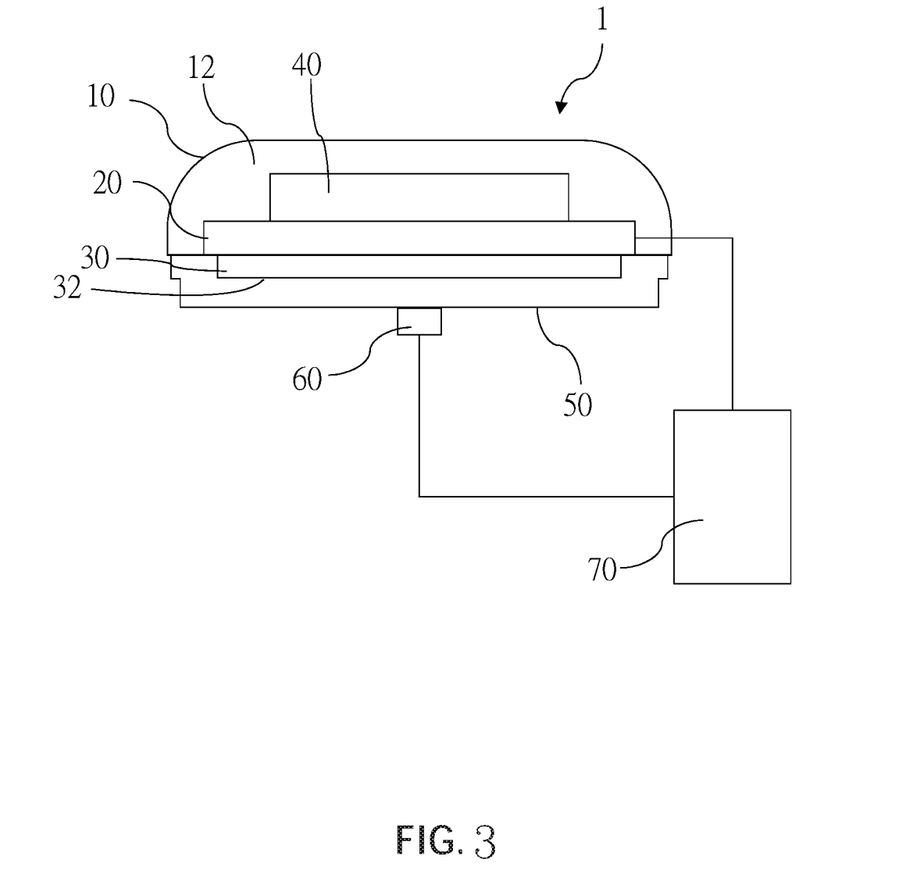
FIG. 3 is a schematic view, showing the light therapy device according to a first embodiment of the present disclosure is connected to the light detector and the test device.

Since the uniform light cover 50 of the light therapy device 1 is adapted to be abutted against the skin surface S, as shown in FIG. 3, in the current embodiment, before the light therapy device 1 is put on the skin surface S, an illumination on an outer surface of the uniform light cover 50 is detected by a light detector 60, thereby to correspond to the illumination for the skin surface S above the illuminated portion T.

Step S04, an illumination corresponding to the skin surface S above the illuminated portion T is measured, and a current output light intensity of the light source 30 is obtained by matching the measured illumination and the corresponding relation in step S03.

In the current embodiment, the test device 70 is connected to the control circuit 20 and the light detector 60 which is located outside of the light therapy device 1. The illumination corresponding to the skin surface S above the illuminated portion T is detected by the light detector 60. The test device 70 matches the illumination detected by the light detector 60 and the relation table, the relation equation, or the relation diagram stored in the memory, thereby to correspondingly obtain the current output light intensity of the light source 30.

Step S05, the light source 30 is controlled by comparing the obtained current output light intensity of the light source 30 and the appropriate intensity range, so that the light intensity outputted by the light source 30 could be in accordance with the appropriate intensity range. In the current embodiment, the test device 70 sends the output light intensity corresponding to the illumination corresponding to the skin surface S above the illuminated portion T to the control circuit 20. The control circuit 20 compares the output light intensity and the appropriate intensity range to generate a comparison result, and controls the light source 30 based on the comparison result. Whereby, the light intensity of the light source 30 could be corrected by detecting the illumination corresponding to the skin surface S above the illuminated portion T to correspondingly adjust the required output light intensity of the light source 30.

In this way, the illumination corresponding to the skin surface S above the illuminated portion T detected by the light detector 60 could be a specific value within the ideal illumination range, and the light intensity outputted by the light source 30 could be a specific value within the appropriate intensity range, thereby to ensure that the light intensity outputted by the light source 30 could allow the illuminated portion T at a specific distance under the skin surface S to be exposed to a suitable light dose. In other words, after the light detector 60 detecting the illumination corresponding to the skin surface S above the illuminated portion T, the corresponding output light intensity is found out, thereby by adjusting the light intensity of the light source 30, the light source 30 could be ensured to output a required output light intensity, and the light source 30 could be ensured to generate the required predetermined illumination within the ideal illumination range, so that the illuminated portion T under the skin surface S could be exposed to an ideal light dose.

In the current embodiment, take r1=1.5 cm, r2=2 cm as an example, calculating based on the equation of step S02, the illuminated time is 3 hours; the rate of light loss at a distance smaller than 1 mm under the skin surface S is 40%; the rate of light loss on the skin surface S of 1-3 mm is 90%; the appropriate intensity range of the light source with a red light wavelength of 630 nm is 0.275-6.6 mW/cm$^2$; the corresponding ideal illumination range is 220-6700 Lux. Preferably, considering that it could be applied to both of the illuminated portion T which is close to the skin surface S and the illuminated portion T which is away from the skin surface S and is under the skin surface S, the appropriate intensity range of the light source is 1.1-1.65 mW/cm$^2$, and the corresponding ideal illumination range is 570-1050 Lux. In this way, by simply adjusting the output light intensity (e.g. light source power) of the light source, the illumination corresponding to the skin surface S above the illuminated portion T could be within the range of 220-6700 Lux, or preferably within the range of 570-1050 Lux, thereby to ensure that the light dose range emitted by the light therapy device 1 of the current embodiment is suitable for the illuminated portion T of the human body.

After removing the test device 70 and the light detector 60 from the light therapy device 1, the light therapy device 1 could be abutted against the skin surface of the human body (as shown in FIG. 1), thereby to provide a light therapy for the illuminated portion T of the human body, and controlling the light source 30 to stop emitting when the illuminated time is reached.

Figure 4:
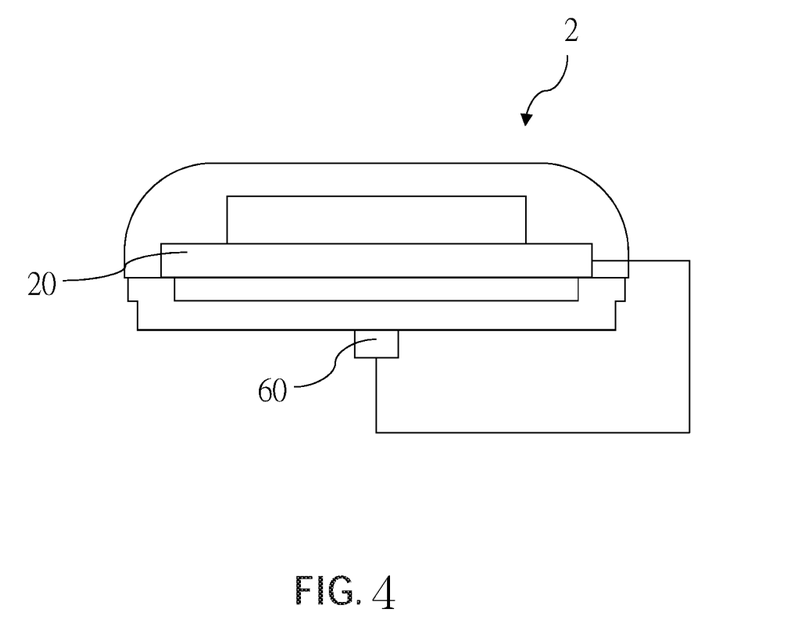
FIG. 4 is a schematic view of the light therapy device according to a second embodiment of the present disclosure.

A light therapy device 2 according to a second embodiment of the present disclosure is illustrated in FIG. 4, which has almost the same structure as that of the first embodiment, except that the corresponding relation between the predetermined illuminations and the predetermined output light intensities is built in a memory in the control circuit 20. In addition, the light detector 60 is detachably connected to the control circuit 20. The control method according to the second embodiment is the same as that of the first embodiment, wherein after the light intensity of the light source is corrected, the light detector 60 is detached from the light therapy device 2.

Figure 5:
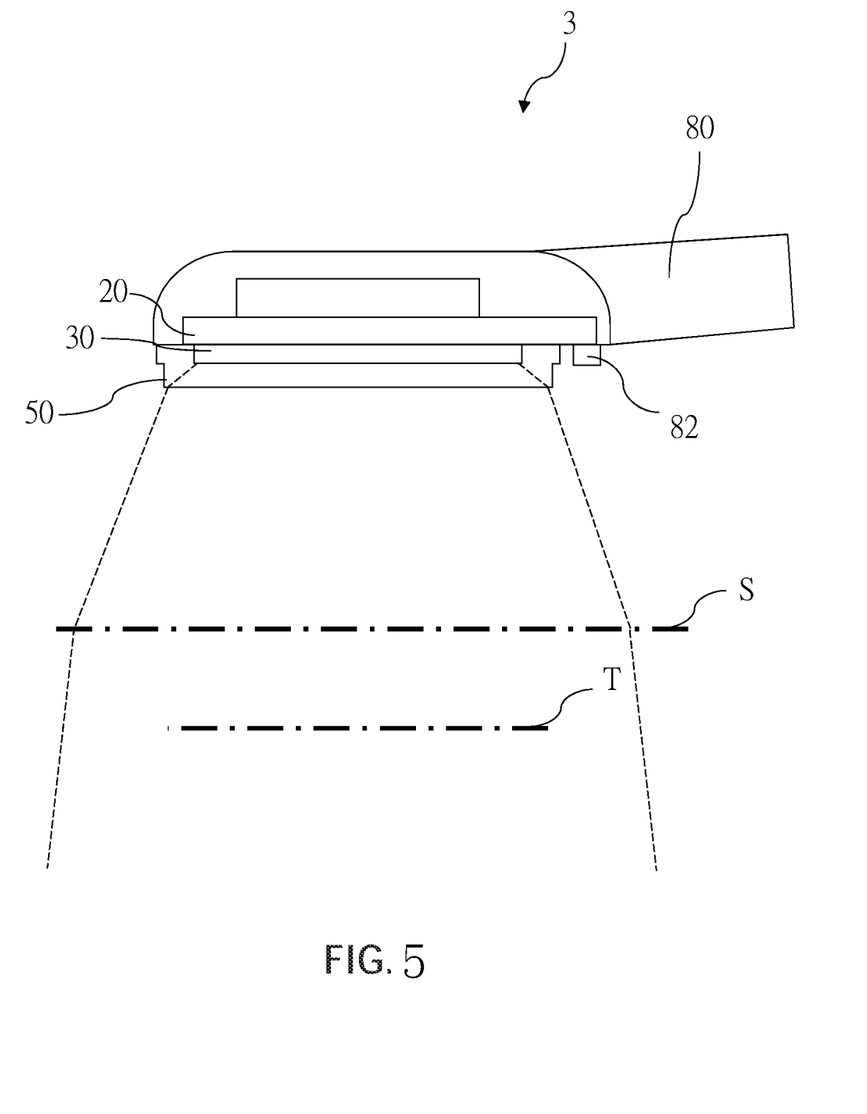
FIG. 5 is a schematic view of the light therapy device according to a third embodiment of the present disclosure.

A light therapy device 3 according to a third embodiment of the present disclosure is illustrated in FIG. 5, which has almost the same structure as that of the aforementioned embodiments, except that the light therapy device 3 is a hand-held light therapy device, and includes a handle 80 which is adapted to be held by a user. In addition, the light therapy device 3 is not abutted against the skin surface S. Since a distance between the light therapy device 3 and the skin surface S varies with different usage habits, in order to keep the illumination corresponding to the skin surface S above the illuminated portion T fixed, thereby to allow the illuminated portion T under the skin surface S to be exposed to a suitable light dose, in the current embodiment, the light therapy device 3 further includes a light detector 82 electrically connected to the control circuit 20, wherein the light detector 82 is adapted to detect an illumination on the skin surface S above the illuminated portion T and sends the illumination back to the control circuit 20.

A control method according to the third embodiment is similar to that of the second embodiment, except that a distance between the skin surface S and the light source 30 is a variable value. Since the ideal light intensity outputted by the light source 30 relates to the distance, and the distance affects the radius or the area of a light beam on the skin surface S which increases (when the distance decreases) or decreases (when the distance increases) the illumination on the skin surface S above the illuminated portion T, in order to keep the illumination on the skin surface S above the illuminated portion T at a fix value, in the current embodiment, step S04 and step S05 are executed when the light source 30 is spaced from the skin surface S by a fix distance (e.g. a distance when the uniform light cover 50 abuts against the skin surface S), thereby to adjust the light intensity of the light source 30 to be in accordance with the appropriate intensity range. At this time, the illumination on the skin surface S above the illuminated portion T is one of the predetermined illuminations within the ideal illumination range corresponding to the fix distance.

After step S05 of the control method of the current embodiment, further comprises a step that the light detector 82 detects the illumination corresponding to the skin surface S above the illuminated portion T (herein defined as another illumination). When the detected another illumination is different from the predetermined illumination within the ideal illumination range corresponding to the fix distance, the control circuit 20 controls the light intensity of the light source 30, thereby to make the another illumination the same as the predetermined illumination corresponding to the fix distance. In this way, when holding the light therapy device 3, the illuminated portion T could be exposed to the same light dose even the distance between the light source 30 and the skin surface S varies.

For example, when the distance between the light source 30 and the skin surface S increases, the another illumination detected by the light detector 82 decreases. At this time, the light detector 82 sends the another illumination back to the control circuit 20, and the control circuit 20 increases the light intensity of the light source 30 based on another corresponding relation which is built in advance, so that the another illumination detected by the light detector 82 is increased to be the same as the predetermined illumination corresponding to the fix distance, wherein the another corresponding relation is a relation between a plurality of illuminations of the light source 30 at different distances and a plurality of light intensities of the light source 30 corresponding to the illuminations at different distances for keeping a fix illumination. By adjusting the output light intensity of the light source 30, the another illumination could be in accordance with the predetermined illumination corresponding to the fix distance. In this way, the illuminated portion T under the skin surface S could be exposed to the same light dose when the distance between the light source 30 and the skin surface S varies.

In addition to controlling the light source 30 based on the another corresponding relation, the another illumination could be used as a feedback, so that the control circuit 20 could instantaneously and correspondingly adjust the light intensity of the light source 30, thereby to keep the another illumination to be in accordance with the predetermined illumination corresponding to the fix distance.

By determining the light dose range required by the illuminated portion, and monitoring the detected illumination corresponding to the skin surface S above the illuminated portion T to be within the ideal illumination range, and controlling the light intensity of the light source to allow the illuminated portion to be exposed to the required light dose, the control method for the light therapy device of the present disclosure could allow the light therapy device to provide a therapeutic performance to the illuminated portion, avoiding unnecessary and ineffective illumination and avoiding damage due to too higher light dose.

It is pointed out that the embodiments described above are only some preferred embodiments of the present disclosure. All equivalent method which employs the concepts disclosed in this specification and recited in the appended claims should fall within the scope of the present invention.

What is claimed is:

1. A control method for a light therapy device, wherein the light therapy device includes a light source; the light source is controllable to change a light intensity outputted by the light source; the control method comprising steps of:
   A. setting a light dose range required by an illuminated portion which is under a skin surface of a human body based on both the illuminated portion below the skin surface and the skin surface, wherein the light dose range is 1-4 J/cm$^2$;
   B. calculating a first light intensity range at a first distance below the skin surface and a second light intensity range at a second distance between the skin surface respectively based on the light dose range, an illuminated time, and a proportion of light beam shape variation between the light source and the skin surface above the illuminated portion, wherein the first distance is smaller than the second distance; taking an upper bound of the first light intensity range as a lower bound of an appropriate intensity range outputted by the light source, and taking a lower bound of the second light intensity range as an upper bound of the appropriate intensity range outputted by the light source, thereby the appropriate intensity range is suitable for both the illuminated portion below the skin surface and the skin surface;
   C. building a corresponding relation between the appropriate intensity range and therapeutic illumination range for the skin surface above the illuminated portion;
   D. measuring an illumination corresponding to the skin surface above the illuminated portion, and correspondingly obtaining an output light intensity of the light source corresponding to the illumination based on the illumination and the corresponding relation; and
   E. controlling the light source based on the output light intensity obtained in step D and the appropriate intensity range in step B whereby the light source outputs the light intensity which is in accordance with the appropriate intensity range to thereby repair tissue in the illuminated portion while minimizing damage to the tissue.

2. The method of claim 1, wherein in step C, the corresponding relation is built by establishing a relation between a plurality of different predetermined illuminations and a plurality of predetermined output light intensities corresponding to the predetermined illuminations; the ideal illumination range includes the predetermined illuminations; the appropriate intensity range includes the predetermined output light intensities; in step D, the illumination corresponding to the skin surface above the illuminated portion corresponds to one of the predetermined illuminations, and the output light intensity corresponds to one of the predetermined output light intensities.

3. The method of claim 2, wherein in step C, each of the predetermined output light intensities and each of the predetermined illuminations are measured during the appropriate intensity range of the light source.

4. The method of claim 2, wherein in step D, the illumination corresponding to the skin surface above the illuminated portion is obtained by measuring an illumination of the skin surface above the illuminated portion when the light source is spaced from the skin surface by a fix distance; after step E, the method further comprises the steps that another illumination of the skin surface above the illuminated portion is measured; when the another illumination is different from one of the predetermined illuminations within the ideal illumination range corresponding to the fix distance, the light intensity of the light source is controlled, thereby to make the another illumination the same as one of the predetermined illuminations corresponding to the fix distance.

5. The method of claim 1, wherein in step B, the appropriate intensity range is 0.275-6.6 mW/cm2; in step C, the therapeutic illumination range is 220-6700Lux.

6. The method of claim 5, wherein in step B, the appropriate intensity range is 1.1-1.65 mW/cm$^2$; in step C, the ideal illumination range is 570-1050Lux.

7. The method of claim 1, wherein in step A, the illuminated portion is a tissue which is under the skin surface; step B further comprises that a specific distance between the illuminated portion and the skin surface is determined, and the corresponding appropriate intensity range is calculated based on the specific distance, the light dose range, the illuminated time, and the proportion of light beam shape variation between the light source and the skin surface above the illuminated portion.

8. The method of claim 7, wherein in step B, the appropriate intensity range is calculated based on a following equation:

$$P = \frac{D_t}{(1-\varepsilon) \times t} \times \left(\frac{r_2}{r_1}\right)^2 \times 1000$$

wherein P is an ideal light intensity of the appropriate intensity range, and a unit thereof is mW/cm$^2$; Dt is a light dose within the light dose range, and a unit thereof is J/cm$^2$; $\varepsilon$ is a rate of light loss at the specific distance under the skin surface; t is the illuminated time; r1 is a radius of a light beam emitted by a light-emitting surface of the light source; r2 is a radius of a light beam on the skin surface above the illuminated portion.

9. The method of claim 7, wherein in step B, the appropriate intensity range is calculated based on a following equation:

$$P = \frac{D_t}{(1-\varepsilon) \times t} \times \frac{A_2}{A_1} \times 1000$$

wherein P is an ideal light intensity of the appropriate intensity range, and a unit thereof is mW/cm$^2$; Dt is a light dose within the light dose range, and a unit thereof is J/cm$^2$; $\varepsilon$ is a rate of light loss at the specific distance under the skin surface; t is the illuminated time; A1 is an area of a light beam emitted by a light-emitting surface of the light source; A2 is an area of a light beam on the skin surface above the illuminated portion.

* * * * *